US00PP34257P2

(12) United States Plant Patent
Kerley

(10) Patent No.: US PP34,257 P2
(45) Date of Patent: May 17, 2022

(54) ***PRIMULA* PLANT NAMED 'KERPOLILA'**

(50) Latin Name: *Primula elatior*
Varietal Denomination: KERPOLILA

(71) Applicant: Kerley & Co. Ltd., Cambridge (GB)

(72) Inventor: David William Kerley, Cambridge (GB)

( * ) Notice: Subject to any disclaimer, the term of this patent is extended or adjusted under 35 U.S.C. 154(b) by 0 days.

(21) Appl. No.: 17/403,377

(22) Filed: Aug. 16, 2021

(51) Int. Cl.
*A01H 5/02* (2018.01)
*A01H 6/00* (2018.01)

(52) U.S. Cl.
USPC ..... Plt./472

(58) Field of Classification Search
USPC ..... Plt./472
See application file for complete search history.

(56) References Cited

PUBLICATIONS https://online.plantvarieties.eu/publicsearch; CPVO Register—CPVO Application Consultation; Retrieved from the Internet on Oct. 18, 2021.*

* cited by examiner

*Primary Examiner* — Susan McCormick Ewoldt
(74) *Attorney, Agent, or Firm* — Cassandra Bright

(57) ABSTRACT

A new and distinct cultivar of *Primula elatior* plant named 'KERPOLILA' is disclosed, characterized by dark lilac double flowers, borne on umbels held above the foliage. This combination is large double flowers on a polyanthus type *Primula* is a novelty. Plants are vigorous and sterile. The new variety is a *Primula elatior*, suitable for outdoor landscape and container use.

2 Drawing Sheets

Figure 1:
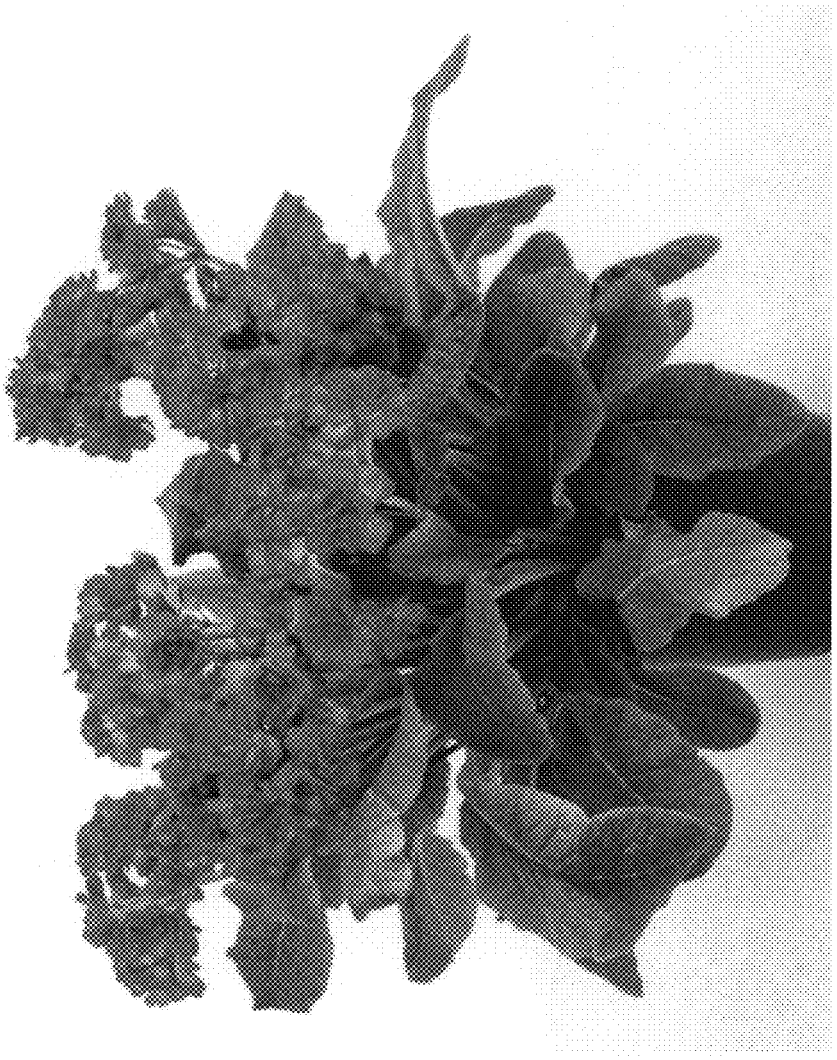

Latin name of the genus and species: *Primula elatior.*
Variety denomination: 'KERPOLILA'.

BACKGROUND OF THE INVENTION

The new cultivar is the product of a planned breeding program under the direction of the inventor, David Kerley. The objective of the breeding program was to produce new *Primula elatior* cultivars with abundant double flowers for commercial ornamental purposes. The new cultivar resulted from crossing of the seed parent, an unpatented, unnamed, proprietary variety of *Primula elatior*, and the pollen parent, a different unnamed, unpatented, proprietary variety of *Primula elatior*. The crossing resulting in the new variety was made in April of 2010 at a research greenhouse in Cambridge, UK. Selection of the new variety 'Kerpolila' was made in March of 2011, by the inventor at a research greenhouse located in Cambridge, UK.

Asexual reproduction of the new cultivar 'KERPOLILA' was first performed in Cambridge, UK during March of 2012, by tissue culture. This and subsequent propagation has shown that the unique features of this cultivar are stable and reproduced true to type in successive generations.

SUMMARY OF THE INVENTION

The cultivar 'KERPOLILA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERPOLILA' These characteristics in combination distinguish 'KERPOLILA' as a new and distinct *Primula* cultivar:

1. Polyanthus type *Primula* with large flowers.
2. Double flowers.
3. Distinctive dark lilac flowers.
4. Flowers borne above foliage on an umbel.
5. Vigorous plants.

PARENT COMPARISON

Plants of the new cultivar 'KERPOLILA' are similar to plants of the seed parent, in most horticultural characteristics. However, plants of the new cultivar differ in the following ways:

1. New cultivar has double flowers; seed parent is single flowered.
2. New variety is sterile; seed parent is fertile.

Plants of the new cultivar 'KERPOLILA' are similar to plants of the pollen parent, in most horticultural characteristics. However, plants of the new cultivar differ in the following ways:

1. New cultivar has double flowers; pollen parent is single flowered.
2. New variety is sterile; seed parent is fertile.

COMMERCIAL COMPARISON

Plants of the new variety can be compared to plants of the *Primula elatior* cultivar 'Kerpolsopin', co-pending application Ser. No. 17/403,358. The inventor is unaware of any other large, doubled-flowered polyanthus type *Primula* with which to compare the new variety. In side-by-side comparisons conducted in Over, Cambridge, United Kingdom, plants of the new *Primula* differed from plants of the cultivar 'Kerpolila' in the following characteristics:

1. The comparator's flower color is near White N155N and Purple N75B; flower color of 'Kerpolila' has a small amount of White N155C, main colors of Purple 77B and 77C with a margin near 77A.

2. Plants of 'Kerpolisopin' are taller than plants of 'Kerpolila'.
3. Foliage of 'Kerpolisopin' is darker green than foliage of 'Kerpolila'.

BRIEF DESCRIPTION OF THE PHOTOGRAPHS

The accompanying photograph in FIG. 1 illustrates in full color a typical plant of 'KERPOLILA' grown in Over, Cambridge, United Kingdom, in a glass-covered greenhouse. This plant was about 7 months old when the photograph were taken. During the production of the plants, day temperatures ranged from 5 to 15 degrees C. and night temperatures ranged from 2 to 12 degrees C.

Figure 2:
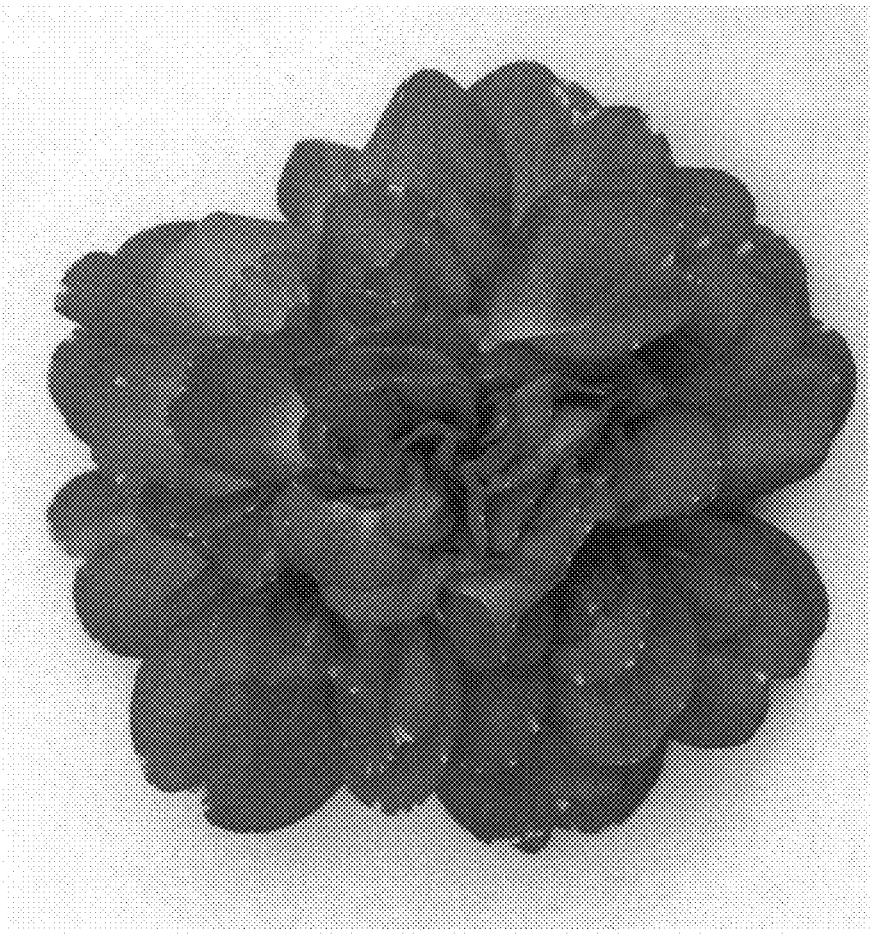

FIG. 2 illustrates a close up of a typical flower of 'KERPOLILA'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2015 except where general terms of ordinary dictionary significance are used. The following observations and measurements describe 'KERPOLILA' plants grown in a greenhouse in Cambridge, United Kingdom. During the production of the plants, day temperatures ranged from 1.5 degrees C. to 25 degrees C. and night temperatures ranged from 1.5 degrees C. to 15 degrees C. No chemical or photoperiodic treatments were given. Measurements were taken during Spring and numerical values represent averages of typical flowering types.

Botanical classification: *Primula elatior* 'KERPOLILA'.

Age of the plant described: Approximately 4 to 5 months in an 11 cm pot.

PROPAGATION

Method: Tissue culture.

Root description: Fibrous, colored near RHS White 155A.

PLANT

Growth habit: Upright, compact and uniform. Flowers borne on umbels above foliage.

Height: Approximately 20 cm.

Plant spread: Approximately 20 cm.

Branching characteristics: No branches, foliage emerges basally.

Vigor: Vigorous.

FOLIAGE

Leaf:

*Arrangement.*—Basal, simple.

*Average length.*—Approximately 16 cm.

*Average width.*—Approximately 6 cm.

*Shape of blade.*—Oblanceolate.

*Apex.*—Obtuse.

*Base.*—Attenuate.

*Margin.*—Slightly crenulate, slightly undulating.

*Texture of top surface.*—Smooth, slightly rugose.

*Texture of bottom surface.*—Rugose with veins prominent.

*Color.*—Developing foliage upper side: Near RHS Yellow-Green 144A. Developing foliage under side: Near RHS Yellow-Green 146C. Mature foliage upper side: Near RHS 137B. Mature foliage under side: Near RHS Yellow-Green 146B.

*Venation.*—Type: Pinnate. Venation color upper side: Near RHS Yellow-Green 148D. Venation color under side: Near RHS Greyed-Green 195C.

Petiole:

*Length.*—Approximately 1 cm.

*Diameter.*—About 5 mm.

*Color.*—Upper Surface: Near RHS Greyed-Green 195C. Lower Surface: Near RHS Greyed-Green 195B. Texture upper surfaces: Glabrous. Texture lower surfaces: Hirsute.

FLOWER

Bloom period: Recurrent flowering during the Spring under United Kingdom outdoor conditions. Very free flowering.

Inflorescence: Umbel. Average diameter range 12 to 14 cm. Average depth 6 cm.

Persistent or self-cleaning: Persistent.

Fragrance: None.

Flowers per inflorescence: 10 to 24 flowers and buds. 5 to 8 inflorescences per plant at one time.

Flower bud:

*Height.*—1.5 cm.

*Diameter.*—6 mm.

*Shape.*—Ovoid.

*Color.*—RHS Purple N74C.

Individual flower:

*Shape and aspect.*—Rotate, double. Upright and outwardly facing.

*Diameter.*—4 cm.

*Depth.*—3 cm.

*Petals.*—48 to 52 per flower, in several concentric whorls.

*Length* (*including tube*).—3.0 cm.

*Width.*—1.4 cm.

*Shape.*—Obcordate.

*Apex.*—Emarginate.

*Margin.*—Entire.

*Texture, upper and lower surfaces.*—Glabrous.

*Color.*—Developing petals, upper surface: Basal region near Yellow 7A (small region, barely visible on undissected flower), then a narrow band of White N155B, before main color of Purple-Violet 81D with a rim of near Purple-Violet 81A. Developing petals, lower surface: Small basal region near Yellow 8D, followed by a narrow band of Yellow-White 158D, then main color near Purple N78D with apex N78A. Mature petals, upper surface: Basal region near Yellow 9A (small region, barely visible on undissected flower), then a narrow band of White N155C, before main color of Purple 77B and 77C with margin near 77A. Mature petals, lower surface: Small basal region near Yellow 4A. Main color near Purple 77B.

*Sepals.*—Quantity per flower: 5 in a single whorl; fused at base. Length: 1.8 cm. Width: 3 mm. Shape: Lanceolate. Apex: Acute. Texture upper surfaces: Glabrous. Texture upper surfaces: Hirsute. Color, upper surface: RHS Yellow-Green 148B. Color, lower surface: RHS Yellow-Green 148C.

Peduncle:

*Peduncle length.*—Average 13 cm. Average range 9 to 17.5 cm.

*Peduncle diameter.*—7 mm.

*Orientation.*—Vertical, straight.

*Strength.*—Strong.

*Color.*—Near RHS Green-White 157A overlaid with Greyed-Purple 184D.

*Texture.*—Hirsute.

Pedicel:

*Pedicel length.*—4 cm.

*Peduncle diameter.*—2 mm.

*Orientation.*—Near vertical on opening flower, dropping to horizontal (90 deg to peduncle) with age in the manner of umbel flower form.

*Strength.*—Moderate.

*Color.*—Near RHS Greyed-Green 195B overlaid with a blush of Greyed-Purple 184D.

*Texture.*—Hirsute.

Bracts:

*Quantity per pedicel.*—1.

*Length.*—1.1 cm.

*Width.*—2 mm.

*Shape.*—Lanceolate.

*Apex.*—Narrowly acute.

*Texture upper surfaces.*—Glabrous.

*Texture upper surfaces.*—Hirsute.

*Color, upper surface.*—RHS Yellow-Green 144B.

*Color, lower surface.*—RHS Yellow-Green 144B.

REPRODUCTIVE ORGANS

Development of reproductive organs has not been observed.

OTHER CHARACTERISTICS

Disease resistance: Plants of the new *Primula* have not been noted to be resistant nor susceptible to pathogens and pests common to *Primula.*

Temperature tolerance: Plants of the new *Primula* have been observed to have tolerated temperatures from about −5 to 28 degrees C.

Fruit/seed production: Fruit and seed production not observed, flowers are sterile.

What is claimed is:

1. A new and distinct cultivar of *Primula* plant named 'KERPOLILA' as herein illustrated and described.

* * * * *